United States Patent [19]
Berg et al.

[11] Patent Number: 4,685,909
[45] Date of Patent: Aug. 11, 1987

[54] DISPOSABLE ABSORBENT ARTICLES

[75] Inventors: Ronald W. Berg, Fairfield; Robert L. Stewart, Cincinnati, both of Ohio

[73] Assignee: The Procter & Gamble Company, Cincinnati, Ohio

[21] Appl. No.: 899,379

[22] Filed: Aug. 22, 1986

Related U.S. Application Data

[63] Continuation-in-part of Ser. No. 734,424, May 15, 1985, abandoned.

[51] Int. Cl.⁴ .............................................. A61F 13/16
[52] U.S. Cl. ..................................... 604/360; 604/375; 536/34
[58] Field of Search .............. 604/359, 360, 367, 368, 604/374, 375, 376, 377, 378; 536/34, 62

[56] References Cited

U.S. PATENT DOCUMENTS

| | | | |
|---|---|---|---|
| 3,004,895 | 10/1961 | Schwartz | 167/84 |
| 3,067,745 | 12/1962 | Burgeni et al. | |
| 3,658,790 | 4/1972 | Bernardin | 260/219 |
| 3,691,154 | 9/1972 | Bernardin | 260/219 |
| 3,707,148 | 12/1972 | Bryce | |
| 3,793,299 | 2/1974 | Zimmerer | 260/2.2 R |
| 3,794,034 | 2/1974 | Jones, Sr. | |
| 3,804,094 | 4/1974 | Manoussos et al. | |
| 3,843,701 | 10/1974 | Wortham | 260/448 R |
| 3,889,678 | 6/1975 | Chatterjee et al. | |
| 3,920,015 | 11/1975 | Wortham | |
| 3,935,862 | 2/1976 | Kraskin | |
| 3,964,486 | 6/1976 | Blaney | |
| 4,020,271 | 4/1977 | Chatterjee | 536/88 |
| 4,055,184 | 10/1977 | Karami | |
| 4,066,584 | 1/1978 | Allen et al. | 260/17.4 CL |
| 4,382,919 | 5/1983 | Alonso et al. | 424/65 |
| 4,610,678 | 9/1986 | Weisman et al. | 604/368 |
| 4,634,438 | 1/1987 | Sustmann et al. | 604/376 |
| 4,634,439 | 1/1987 | Sustmann et al. | 604/376 |

FOREIGN PATENT DOCUMENTS

| | | |
|---|---|---|
| 57-45057 | 3/1982 | Japan. |
| 58-104276 | 6/1983 | Japan. |
| 748135 | 4/1956 | United Kingdom. |

OTHER PUBLICATIONS

The Newton Kansan, "Distribution Ready," Sep. 8, 1984.
Nite Comfort TM Diaper Rash Buffer, undated product brochure.
Kaj Health Products, Inc., Press Release, "To Control & Prevent Diaper Rash," May 13, 1985.

*Primary Examiner*—John D. Yasko
*Attorney, Agent, or Firm*—George W. Allen; Steven J. Goldstein; Jack D. Schaeffer

[57] ABSTRACT

Absorbent articles containing both pH control agents and substantially water-insoluble, highly neutralized hydrogel material as a fluid-absorbing polymer are disclosed. By placing pH control agents and hydrogel in distinct discrete zones within the article, absorbent products such as diapers can be realized which are highly effective for absorbing discharged body fluids and which also serve to prevent or reduce diaper rash.

39 Claims, 4 Drawing Figures

DISPOSABLE ABSORBENT ARTICLES

CROSS REFERENCE TO RELATED APPLICATION

This application is a continuation-in-part of the application having Ser. No. 734,424, filed May 15, 1985 in the names of Ronald W. Berg and Robert L. Stewart, now abandoned.

FIELD OF THE INVENTION

The present invention relates to disposable absorbent articles such as diapers and incontinence pads. Such articles are assembled in a manner which renders them especially effective for absorbing discharged body fluids while at the same time preventing or reducing diaper rash.

BACKGROUND OF THE INVENTION

Diaper rash is a common form of irritation and inflammation of those parts of an infant's body normally covered by a diaper. This condition is also referred to as diaper dermatitis, napkin dermatitis, napkin rash, and nappy rash. While certainly more common in infants, this condition is not, in fact, limited to infants. Any individual who suffers from incontinence may develop this condition. This ranges from newborns, to the elderly, to critically ill or nonambulatory individuals.

It is generally accepted that true "diaper rash" or "diaper dermatitis" is a condition which is, in its most simple stages, a contact irritant dermatitis. The irritation of simple diaper rash results from extended contact of the skin with urine, or feces, or both. Diapers are worn to catch and hold the body waste, but generally hold the waste in direct contact with the skin until changed, i.e., in occluded fashion for long periods of time. The same is true for an incontinence pad, or incontinence brief. However, while it is known that the body waste "causes" diaper rash, the precise component or components of the urine or feces which are responsible for the resulting irritation of the skin have not been conclusively identified. The most commonly accepted list of factors linked to diaper rash includes ammonia, bacteria, the products of bacterial action, urine pH, *Candida albicans,* and moisture. These are generally cited in the art as being the most likely candidates for agents or conditions which produce or aggravate diaper rash.

It has now been discovered that a primary cause of diaper rash is a particular set of conditions which arises as a result of prolonged contact of skin with mixtures of feces and urine. Activity of proteolytic and lipolytic fecal enzymes present in such a mixture is believed to be a major factor in producing skin irritation. Urine in contact with enzymes from feces can also result in production of ammonia which raises skin pH. This rise in skin pH, for example to levels of 6.0 and above, in turn increases that fecal proteolytic and lipolytic enzymatic activity which produces diaper rash. Urine itself can also contribute to diaper rash by adding moisture to the diaper environment. Water, and particularly water in the form of urine, is especially effective at diminishing the barrier property of skin, thereby enhancing the susceptibility of skin to fecal enzyme irritation. However, when skin pH is kept between about 3.0 and 5.5, the skin's barrier properties can be maintained. The foregoing diaper rash model suggests that effective diaper rash control can be achieved by maintaining skin pH well within the acidic range to inhibit irritation-producing enzymatic activity while simultaneously maintaining the diaper environment as dry as possible.

Articles, compositions and procedures which inherently tend to lower the pH of diapered skin are known in the art. In fact, a number of prior art references teach the addition of various acidic pH control or "ammonia-absorbing" agents to diapers or to the diapered skin environment. Such references include, for example, Alonso et al., U.S. Pat. No. 4,382,919, Issued May 10, 1983; Blaney, U.S. Pat. No. 3,964,486, Issued June 22, 1976; Bryce, U.S. Pat. No. 3,707,148, Issued Dec. 26, 1972; and Jones, Sr., U.S. Pat. No. 3,794,034, Issued Feb. 26, 1974.

Likewise, a number of prior art references describe absorbent articles which are said to be especially effective in absorbing urine and maintaining skin dryness. Frequently such articles involve the utilization of superabsorbent polymeric material, such as water-insoluble, slightly cross-linked hydrogel or hydrocolloid material, that absorbs and holds many times its weight in discharged fluid. References involving the use of such superabsorbent polymers in diaper structures include, for example, Harper et al., U.S. Pat. No. 3,669,103, Issued June 13, 1972; Harmon, U.S. Pat. No. 3,670,731, Issued June 20, 1972; Masuda et al., U.S. Pat. No. 4,076,663, Issued Feb. 28, 1978; Melican, U.S. Pat. No. 4,232,674, Issued Nov. 11, 1980; Holtman, U.S. Pat. No. 4,333,463, Issued June 8, 1982; Mazurak et al., U.S. Pat. No. 4,381,782, Issued May 3, 1983 and Elias, U.S. Pat. No. 4,381,783, Issued May 3, 1983.

None of the foregoing prior art references provide both especially effective skin pH control agents and especially effective moisture-absorbing hydrogel polymers in the same absorbent structure. In fact, simple combination of acidic pH control agents with superabsorbent polymer material in the same structure cannot be accomplished without some difficulty. The preferred moisture-absorbing hydrogel materials are not especially effective fluid absorbers under low pH conditions. The presence of acidic skin pH control agents, which lower pH conditions in the region of hydrogel-moisture contact, thus tends to diminish the moisture-absorbing effectiveness of the hydrogel materials. There is therefore a need to identify preferred structures and configurations for absorbent articles which contain both effective acidic pH control agents and effective moisture-absorbing hydrogel polymers such that each of these components can efficiently contribute to the prevention or reduction of diaper rash. It has not been discovered that improved diaper rash-reducing absorbent articles containing both acidic pH control agents and moisture-absorbing, highly neutralized hydrogel can be realized by incorporating these materials into distinct zones or areas within the absorbent article structure.

SUMMARY OF THE INVENTION

The present invention provides an absorbent article, such as a diaper or incontinence pad, which is suitable for absorbing body fluids while at the same time reducing or preventing diaper rash. Such an absorbent article comprises a liquid impervious backing sheet, a relatively hydrophobic, liquid pervious topsheet, a flexible absorbent core positioned between the backing sheet and the topsheet, and one or more pH control agents suitable for maintaining skin pH within the range of from about 3.0 to 5.5 in the presence of urine and feces.

The flexible absorbent core used in the structure comprises both hydrophilic fiber material and particles of substantially water-insoluble, highly neutralized hydrogel material. Such hydrogel material is considered to be highly neutralized if at least 50% of the acidic functional groups of the hydrogel material are neutralized with salt-forming cations.

The particles of the hydrogel material and the pH control agents are non-uniformly distributed in distinct discrete zones within the absorbent article. Such separation of hydrogel and pH control agents can be accomplished, for example, by incorporating the pH control agent with the topsheet of or an insert for the article and not in the hydrogel-containing absorbent core. Alternatively, both pH control agent and hydrogel may be present in the absorbent core but in separate and/or distinct layers of the core or in separate zones of the core as defined by distinct sections of the core surface. By separating hydrogel material and pH control agents in this manner, skin pH control to combat diaper rash can be realized without adversely affecting the ability of the highly neutralized hydrogel material to absorb fluids and maintain requisite skin dryness.

DETAILED DESCRIPTION OF THE INVENTION

Figure 1:
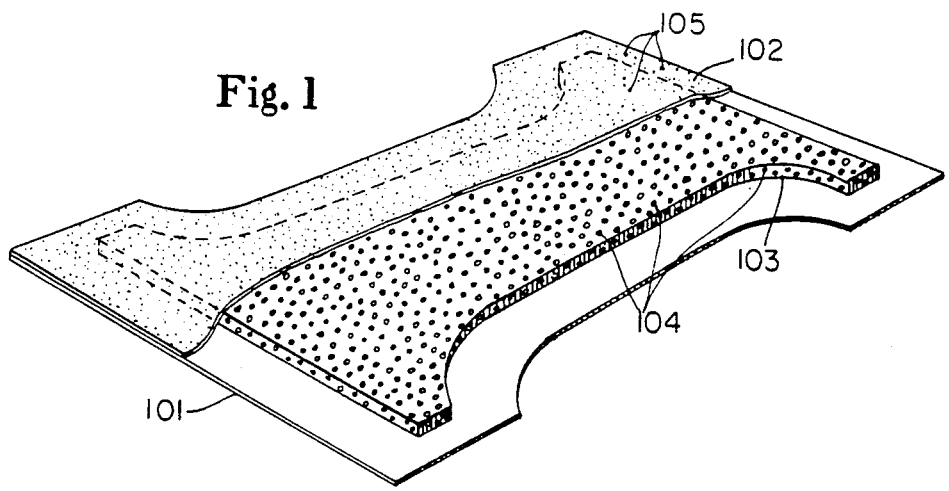
FIG. 1 represents a cut-away view of a diaper structure having acidic pH control agent carried by the topsheet.

The absorbent articles of the present invention can be manufactured in the configuration of wearable disposable products which are capable of absorbing significant quantities of water and body waste fluids such as urine and feces. Thus such articles, for example, may be prepared in the form of disposable diapers, adult incontinence pads and the like.

The absorbent articles herein generally comprise three basic structural components. One such component is a liquid impervious backing sheet. On top of this backing sheet is placed an absorbent core which may itself comprise one or more distinct layers. On top of this absorbent core is placed a relatively hydrophobic, liquid pervious topsheet. The topsheet is the element of the article which is placed next to the skin of the wearer. In one embodiment, described more fully hereinafter, the articles herein will include as a fourth element a flexible substrate, e.g., an insert, containing acid pH control agent. Such an insert can be placed on top of the topsheet next to the skin of the wearer.

Especially preferred absorbent articles of this invention are disposable diapers. Articles in the form of disposable diapers are fully described in Duncan and Baker, U.S. Pat. No. Re. 26,151, Issued Jan. 31, 1967; Duncan, U.S. Pat. No. 3,592,194, Issued July 13, 1971; Duncan and Gellert, U.S. Pat. No. 3,489,148, Issued Jan. 13, 1970; and Buell, U.S. Pat. No. 3,860,003, Issued Jan. 14, 1975; which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. The backsheet most preferably has a width greater than that of the core thereby providing side marginal portions of the backsheet which extend beyond the core. The diaper is preferably constructed in an hourglass configuration.

The backsheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the article herein can be made in part or completely of synthetic fibers such as polyester, polyolefin, rayon, or the like, or of natural fibers such as cotton. The fibers are typically bound together by a thermal binding procedure or by a polymeric binder such as polyacrylate. This sheet is substantially porous and permits a fluid to readily pass therethrough into the underlying absorptive core. The topsheet can be made more or less hydrophobic depending upon the choice and treatment of fiber and binder used in the construction thereof. The topsheets used in the articles of the present invention are relatively hydrophobic in comparison with the absorbent core of said articles. Topsheet construction is generally disclosed in Davidson, U.S. Pat. No. 2,905,176, Issued Sept. 22, 1959; Del Guercio, U.S. Pat. No. 3,063,452, Issued Nov. 13, 1962; and Holliday, U.S. Pat. No. 3,113,570, Issued Dec. 10, 1963, which patents are incorporated herein by reference. Preferred topsheets are constructed from polyester, rayon, rayon/polyester blends or polypropylene.

An absorbent core, which may itself comprise one or more separate and/or distinct zones, e.g., layers, is positioned between the backing sheet and the topsheet to form the absorbent articles herein. Such an absorbent core comprises, at least in part, a mixture of hydrophilic fiber material and particles of substantially water-insoluble, highly neutralized hydrogel material. This mixture will generally be in the form of a web of the hydrophilic fibers with the discrete particles of hydrogel dispersed therein.

The type of hydrophilic fibers is not critical for use in the present invention. Any type of hydrophilic fiber which is suitable for use in conventional absorbent products is also suitable for use in the absorbent structure of the present invention. Specific examples of such fibers include cellulose fibers, rayon, polyester fibers. Other examples of suitable hydrophilic fibers are hydrophilized hydrophobic fibers, such as surfactant-treated or silica-treated thermoplastic fibers. Also, fibers which do not provide webs of sufficient absorbent capacity to be useful in conventional absorbent structures, but which do provide good wicking properties, are suitable for use in the absorbent structures of the present invention. This is so because, in the presence of hydrogel particles, wicking properties of the fibers are far more important than their absorbent capacity. For reasons of availability and cost, cellulose fibers, in particular wood pulp fibers, are preferred.

As indicated, absorbent cores formed from such hydrophilic fibers also contain discrete particles of substantially water-insoluble, highly neutralized hydrogel material. Such highly neutralized hydrogel materials are those organic compounds capable of absorbing aqueous fluids and retaining them under moderate pressures. For good results, the hydrogels must be substantially water insoluble.

Examples of such hydrogels include material in the form of cross-linked polymers. Cross-linking may be by covalent, ionic, vander Waals, or hydrogen bonding. Examples of hydrogel polymers include ethylene maleic anhydride copolymers, carboxymethylcellulose, polymers and copolymers of vinyl sulfonic acid, polyacrylates, and the like. Other suitable hydrogels are those disclosed in Assarsson et al., U.S. Pat. No. 3,901,236, Issued Aug. 26, 1975, the disclosure of which is incorporated herein by reference. Particularly preferred polymers for use herein are acrylic acid grafted starch, polyacrylates, and isobutylene maleic anhydride copolymers, or mixtures thereof.

Processes for preparing hydrogels are disclosed in Fusayoshi Masuda et al., U.S. Pat. No. 4,076,663, Issued Feb. 28, 1978; in Tsuno Tsubakimoto et al., U.S. Pat. No. 4,286,082, Issued Aug. 25, 1981; and further in U.S. Pat. Nos. 3,734,876, 3,661,815, 3,670,731, 3,664,343, 3,783,871, and Belgian Pat. No. 785,858, the disclosures of all of which patents are incorporated herein by reference.

The hydrogel materials used in the present invention are highly neutralized hydrogels and therefore must be hydrogels which contain neutralizable, acidic functional groups. Thus these hydrogels must be polymers prepared from at least some monomers containing at least one carboxylic acid, carboxylic acid anhydride or sulfonic acid group. Generally at least 10 mole percent and more preferably at least 50 mole percent of the hydrogel structure will be prepared from such acid group-containing monomers.

The hydrogel material essentially used in the absorbent core of the articles herein is highly neutralized, i.e. at least 50%, and preferably at least 65% of the hydrogel acidic functional groups must be neutralized with a salt-forming cation. Sutiable salt-forming cations include alkali metal, ammonium, substituted ammonium and amines. Neutralization can be carried out either before or after polymerization of the acid group-containing hydrogel material has occurred. Neutralization can be accomplished in known manner using conventional techniques. It should be understood that the hydrogel material employed in the present invention must be neutralized to the extent of at least 50% prior to contact of the hydrogel material with body fluids such as urine.

Hydrogel material is used in the form of discrete particles in the absorbent core of the absorbent articles herein. Such particles can be of any desired shape, e.g., spherical or semi-spherical, cubic, rod-like, polyhedral, etc. Shapes having a large greatest dimension/smallest dimension ratio, like needles, flakes and fibers, are also contemplated for use herein. Conglomerates of hydrogel particles may also be used.

Although the absorbent cores of the present invention are expected to perform well with hydrogel particles having a particle size varying over a wide range, other considerations may preclude the use of very small or very large particles. For reasons of industrial hygiene, (weight) average particle sizes smaller than about 30 microns are less desirable. Particles having a smallest dimension larger than about 3 mm may also cause a feeling of grittiness in the absorbent structure, which is undesirable from a consumer aesthetics standpoint. Preferred for use herein are particles having an (weight) average particle size of from about 50 microns to about 1 mm. "Particle Size" as used herein means the weight average of the smallest dimension of the individual particles.

The relative amount of hydrophilic fibers and hydrogel particles used in the highly neutralized hydrogel-containing portion of the cores of the absorbent articles herein can be most conveniently expressed as a weight ratio of fiber to hydrogel. These ratios may range from about 30:70 to about 98:2. Low fiber/hydrogel ratios, i.e., from about 30:70 to about 50:50, are practicable only when the hydrogel used possesses a low swelling capacity i.e., hydrogels having an absorbent capacity for urine and other body fluids of less than about 15 times their own weight (15×). (Absorbent capacity data are generally available from the manufacturer of the hydrogel or may conveniently be determined by known means.) Hydrogels which have a very high absorption capacity (e.g., 25×, and which consequently exhibit a high degree of swelling after wetting) tend to gel block when used in absorbent structure cores at low fiber/hydrogel ratios. This phenomenon causes undesirable, slow, diffusion type absorption kinetics. Very high fiber/hydrogel ratios, e.g. above 95:5, on the other hand, provide meaningful performance benefits only if the hydrogel used has a high absorbent capacity (e.g., 25× for urine and other body fluids). For most commercially available hydrogels the optimum fiber/hydrogel ratio is in the range of from about 50:50 to about 95:5.

Based on a cost/performance analysis, fiber/hydrogel ratios of from about 75:25 to about 90:10 are preferred. This preference is, of course, based on the relative costs of hydrophilic fibers (e.g. wood pulp fibers) and hydrogel. If, for example, wood pulp prices would go up and/or hydrogel prices would come down, lower fiber/hydrogel ratios would be more cost effective.

The density of the hydrogel-containing portion of the absorbent structure core is of some importance in determining the absorbent properties of the resulting absorbent structure. When hydrogel particles are dispersed into an absorbent web of hydrophilic fibers having a density of about 0.1 g/cm$^3$, the admixture of the hydrogel results in only a small increase in the amount of fluid which is absorbed within a practicably reasonable time (e.g. 10 minutes) because the fluid uptake of such webs is slow. When the hydrogel-containing absorbent core is densified to a density of at least about 0.12 g/cm$^3$, a marked increase in absorbent capacity is observed. It is believed that densifying the web results in better wicking of fluid into the web, so that more hydrogel particles participate in the absorption process, which results in a higher actual absorbent capacity. It is further believed that a densified web may be more effective in keeping the hydrogel particles isolated from each other. Densifying the web further, from about 0.15 g/cm$^3$ to about 1 g/cm$^3$, results in a reduction in the bulk of the structure (which is desirable from a consumer standpoint, for aesthetics reasons), without loss of absorbent capacity. However, above a density of about 0.6 g/cm$^3$, further densification hardly reduces the bulk further, because of the inverse relationship between bulk and density. The density of the portion of the absorbent core containing highly neutralized hydrogel particles is therefore preferably in the range of from about 0.10 to about 0.6 g/cm$^3$, and more preferably within the range of from about 0.12 to about 0.25 g/cm$^3$.

The portion of the absorbent core which contains the highly neutralized hydrogel can be formed by airlaying a dry mixture of hydrophilic fibers and hydrogel particles. Such a procedure is described more fully in Procter & Gamble; European Patent Publication No. EP-A-122042; Published Oct. 17, 1984, incorporated herein by reference. As indicated in this reference, the webs formed by this procedure for use in the articles herein will preferably comprise substantially unbonded fiber and will preferably have a moisture content of 10% or less.

As noted hereinbefore, the web formed from a mixture of hydrophilic fibers and the highly neutralized hydrogel particles need form only a portion of the total absorbent core used in the absorbent articles of this invention. Other sections or zones of the absorbent core can contain no hydrogel particles and may comprise only hydrophilic fibers or may comprise pH control agents, with or without hydrophilic fibers, as hereinafter more fully described. Such distinct core sections can comprise separate and/or distinct layers within the absorbent core or can comprise separate and/or distinct areas or zones within the same layer.

In a preferred diaper embodiment of the present invention, the absorbent core with all its distinct sections taken together, will be hourglass shaped, i.e., the width of the center of the core is substantially less than the width of the core at the ends. In a preferred diaper embodiment, the absorbent core with all its distinct sections and layers will have a total thickness within the range of from about 5 mm to 20 mm, more preferably from about 7 mm to 12 mm.

Another essential feature of the present invention is the presence in the absorbent articles herein of one or more pH control agents. Such agents are non-uniformly distributed within the absorbent article and are placed in discrete zones within the article. These zones containing pH control agent are substantially distinct from the zones wherein the highly neutralized hydrogel particles are placed.

The useful pH control agents are those which maintain skin pH within the range of from about 3.0 to 5.5, and preferably from about 3.5 to 4.5 in the presence of urine and feces. Preferably skin pH is maintained within this range for the length of time the diaper is worn, e.g., for at least 4 hours for daytime infant diapers and for at least 8 hours for nighttime infant diapers.

A wide variety of non-toxic, non-irritating acidic materials which release protons can serve as skin pH control agents. Thus these materials can be low molecular weight organic or inorganic acids, high molecular weight polymeric acids or ion exchange resins and fibers in the hydrogen form.

Suitable low molecular weight organic and inorganic acid materials include such weak acids as citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid and acid phosphate salts. These low molecular weight materials may be used in combination with their conjugate bases to provide buffer capacity. Some of these acid materials, such as adipic acid, possess inherent buffering capacity as a result of their relative limited water solubility.

Suitable high molecular weight polymeric acids include polyacrylic acid and its polyacrylate derivatives, poly(maleic acid) and its polymaleate derivatives, alginic acid, carboxymethylcellulose and the like. Polyacrylic acid and its polyacrylate derivatives useful as pH control agents may be cross-linked or uncross-linked and may range in molecular weight from 1,000 to 5,000,000. Such acrylic acid-based materials include, for example, the Carbopol resins which are water-soluble polymers of acrylic acid cross-linked with such materials as polyallyl sucrose and polyallyl pentaerythritol. Poly(maleic acid) and its polymaleate derivatives useful as pH control agents may also be cross-linked or uncross-linked and may range in molecular weight from 1,000 to 5,000,000. Poly(maleic acid) derivatives include poly(vinyl ether-maleic acid), and poly(methyl vinyl ether-maleic acid) such as the resins and poly (styrene-maleic acid) materials.

All of the foregoing higher molecular weight polymeric materials, unlike the highly neutralized hydrogel absorbent polymers used in the present invention, must be less than 50% neutralized and thus predominately in the free acid form to be effective as pH control agents in the absorbent articles herein.

One preferred type of pH control agent comprises polyacrylic acid and polyacrylic acid derivatives. These preferred polyacrylic acid derivatives can include the same type of starch-grafted polyacrylic acid or polyacrylate materials as the highly neutralized hydrogel materials used as absorbents in the present invention. Such acidified hydrogel materials indeed do possess some degree of fluid absorbing capacity in addition to their capacity to lower skin pH. It should be noted, however, that when materials of this type are used as pH control agents in the absorbent articles herein, they must be less than 50% neutralized. Thus, in the context of the present invention, such acidified hydrogels must always be used in combination with the more absorbent, more fully neutralized hydrogels hereinbefore described as the essential fluid-absorbing hydrogel element of the articles herein.

Another preferred type of pH control agent comprises ion exchanging, modified cellulose materials in fiber form. This includes, for example, carboxymethylcellulose in the free acid form, oxidized cellulose, sulfoethyl cellulose and phosphorylated cellulose ("cellulose phosphate") prepared by conventional techniques. Phosphorylated cellulose, for example, can be prepared by treating cellulose with solutions of urea and phosphoric acid, with phosphorus oxychloride and pyridine, with phosphorus oxychloride and phosphoric acid, with phosphorus oxychloride and dioxane or with phosphorus oxychloride alone. Examples of methods for preparing phosphorylated cellulose ion-exchanging fibers are described in Bernardin, U.S. Pat. No. 3,691,154, Issued Sept. 12, 1972, and Bernardin, U.S. Pat. No. 3,658,790, Issued Apr. 25, 1972. Methods for preparing other types of ion-exchanging cellulose derivatives are described in Sano et al., U.S. Pat. No. 4,200,735, Issued Apr. 29, 1980, Ward et al., U.S. Pat. No. 3,854,868, Issued Dec. 17, 1974 and Bridgeford, U.S. Pat. No. 3,533,725, Issued Oct. 13, 1970. All of the foregoing patents are incorporated herein by reference.

Modified cellulose ion-exchanging fibers for use in their hydrogen form as pH control agents in the present invention preferably have an ion-exchange capacity of at least about 0.4 meq./gram, more preferably at least about 1.0 meq./gram. Cellulose-derived pH control agents are especially advantageous for incorporation into the absorbent core of the articles herein since such acidic ion-exchanging fibers can easily be admixed with the hydrophilic fibers essentially present in the absorbent core.

The pH control agents of whatever type used in the absorbent articles of the present invention will generally comprise from about 1% to 30% by weight of the total absorbent article. More preferably, such agents can comprise from about 5% to 15% by weight of the article.

It has been discovered that the moisture-absorbing hydrogel material and the acidic skin pH control agents hereinbefore described can be successfully and usefully incorporated into the same absorbent article provided such hydrogel particles and pH control agents are non-uniformly distributed in distinct discrete zones within the absorbent article. For purposes of the present invention, highly neutralized hydrogel and pH control agents are deemed to be non-uniformly distributed in the absorbent article when there is (a) at least one zone (and generally no more than ten zones) within the article wherein the weight ratio of hydrogel to pH control agent is at least about 10:1, and (b) at least one zone (and generally no more than ten zones) within the article wherein the weight ratio of pH control agent to hydrogel is at least about 10:1.

Such non-uniform distribution of the highly neutralized hydrogel and pH control agent can be accomplished in a number of ways. In one embodiment, the pH control agent is distributed in or on the topsheet of the absorbent article with little or no pH control agent being placed in the hydrogel-containing absorbent core of the article. An article of this type is described in FIG. 1 of the drawings submitted herewith. This hourglass-shaped diaper structure comprises a liquid impervious backing sheet 101 and a hydrophobic topsheet 102. Positioned between the backing sheet and topsheet is an hourglass-shaped absorbent core 103 containing hydrophilic fiber material such as wood pulp fiber. Also distributed throughout the absorbent core 103 are discrete particles 104 of substantially water-insoluble, highly neutralized hydrogel material. Acid pH control agent 105 suitable for maintaining skin pH between 3.0 and 5.5 is coated on or impregnated in the topsheet 102 and is thus maintained in a distinct zone from the hydrogel particles 104 in the diaper core.

In another embodiment, both highly neutralized hydrogel and pH control agent may be placed in the absorbent core but in distinct discrete zones within the core. Such separation, for example, may be effected by placing hydrogel and pH control agent in different layers of the core. Thus one layer of the core, preferably the top layer, can comprise hydrophilic fiber material and pH control agent in a weight ratio of fiber to agent of from about 10:1 to 1:1, with substantially no highly neutralized absorbent hydrogel present. Another layer of the core, preferably the bottom layer, can comprise hydrophilic fiber and highly neutralized hydrogel material in a weight ratio of fiber to highly neutralized hydrogel of from about 10:1 to 1:1, with substantially no pH control agent present.

Figure 2:
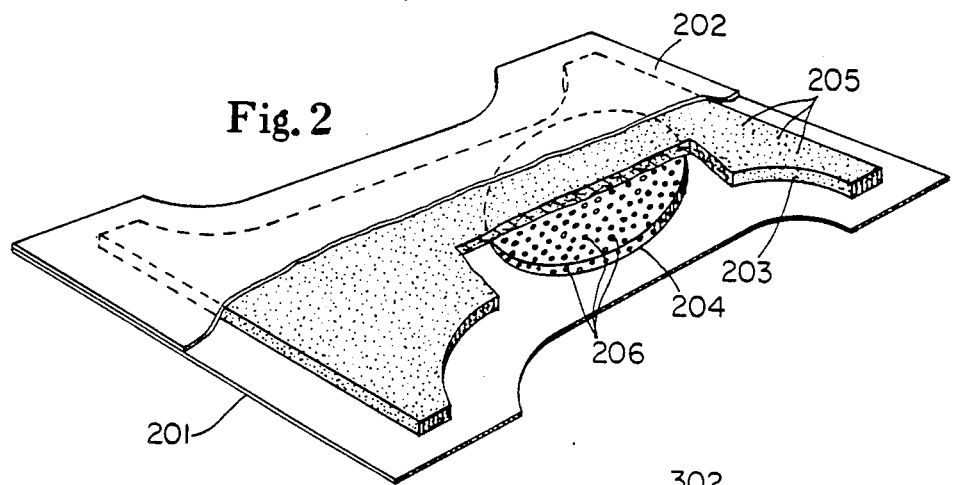
FIG. 2 represents a cut-away view of a diaper structure having a dual-layer absorbent core comprising both an upper layer containing acid pH control agent and a separate lower insert layer containing hydrogel particles.

A diaper article with such a layered core is depicted in FIG. 2 of the drawings submitted herewith. This hourglass-shaped diaper structure also comprises a liquid impervious backing sheet 201 and a hydrophobic topsheet 202. The absorbent core of the structure comprises two distinct layers, i.e., an upper, hourglass-shaped layer 203 and a lower, oval insert layer 204. The upper layer 203 contains pH control agent 205 admixed therewith. The lower oval insert layer 204 contains discrete particles 206 of substantially water-insoluble, highly neutralized hydrogel distributed throughout this lower oval insert layer.

In yet another embodiment, the absorbent core of the article may comprise three distinct layers with one layer, preferably the top, consisting essentially of hydrophilic fiber plus pH control agent, another layer, preferably the bottom, consisting essentially of hydrophilic fiber plus highly neutralized hydrogel and a third layer, preferably positioned between the other two layers, consisting essentially of hydrophilic fibers only.

In yet another embodiment, the discrete zones containing, respectively, pH control agent and highly neutralized hydrogel material, may comprise different portions of the absorbent article or core thereof as defined by partitioning the flat surface of the article or core into at least one area of relatively high hydrogel concentration and at least one area of relatively high pH control agent concentration. For example, the front two-thirds section of the absorbent article, as viewed unfolded from the top, may contain substantially all of the highly neutralized hydrogel material whereas the back or rear one-third section of the article may contain substantially all of the pH control agent. Size and shape of the discrete zones of high pH control agent concentration and high hydrogel concentration can, of course, vary according to the intended use and size requirements of the absorbent article desired.

Figure 3:
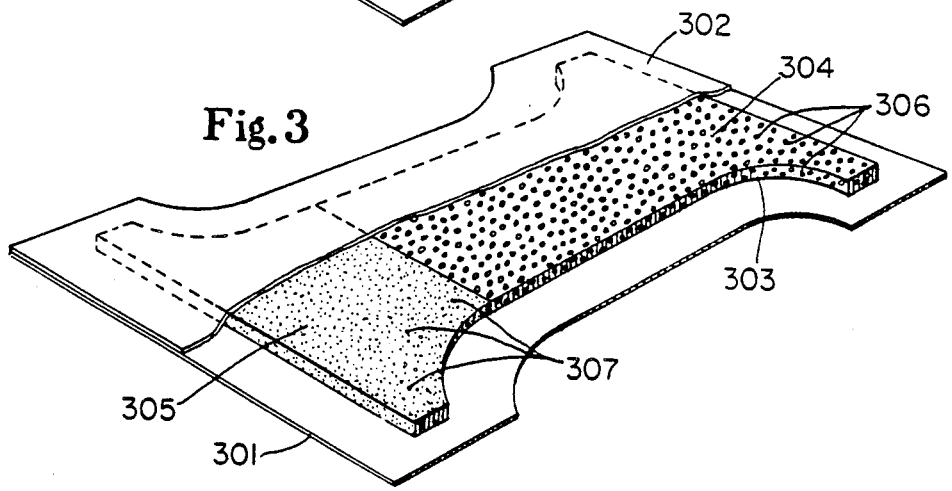
FIG. 3 represents a cut-away view of a diaper structure having its absorbent core partitioned into distinct sections containing, respectively, hydrogel and acid pH control agent.

A diaper article with hydrogel and pH control agent in separate sections of the same absorbent core layer is depicted in FIG. 3 of the drawings submitted herewith. This hourglass-shaped structure also comprises a liquid impervious backing sheet 301 and a hydrophobic topsheet 302. A hydrophilic fiber-containing absorbent core 303 is positioned between the backing sheet 301 and topsheet 302. The absorbent core 303 in this embodiment comprises a hydrogel-containing zone 304 consisting of the front two-thirds of the absorbent core 303 and a pH control agent-containing zone 305 consisting of the back one-third of the absorbent core 303. Discrete particles 306 of substantially water-insoluble, highly neutralized hydrogel are distributed throughout the hydrogel-containing zone 304. Acidic pH control agent 307 is distributed throughout the pH control agent-containing zone 305.

In yet another embodiment, the pH control agent may be incorporated on or in a water-insoluble, flexible substrate which is positioned on top of the topsheet of the absorbent article next to the wearer's skin. The highly neutralized hydrogel particles are incorporated into the absorbent core of the article in conventional fashion. In this manner the requisite separation of pH control agents and hydrogel particles can be realized.

Figure 4:
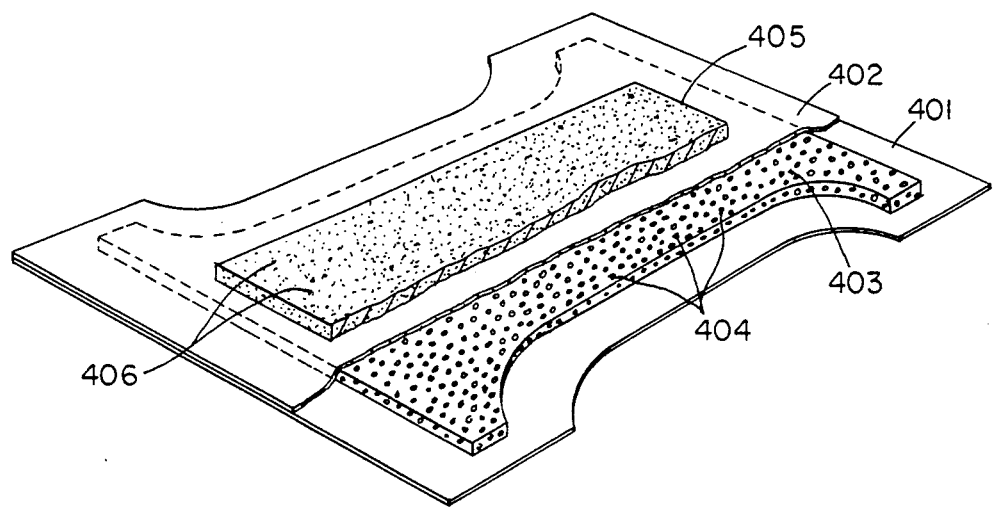
FIG. 4 represents a cut-away view of a diaper structure having acid pH control agent-containing insert positioned on top of the diaper topsheet so that such an insert will be in contact with the wearer's skin.

A diaper article with such an acid-containing insert positioned on the topsheet is shown in FIG. 4. This hourglass-shaped diaper also comprises a liquid impervious backing sheet 401 and a hydrophobic, liquid pervious topsheet 402. Positioned between the backing sheet and topsheet is an hourglass-shaped absorbent core 403 containing hydrophilic fiber material such as wood pulp fiber. Distributed throughout the absorbent core 403 are discrete particles 404 of substantially water-insoluble, highly neutralized hydrogel material. Positioned on top of the topsheet is a rectangular flexible substrate 405 which has impregnated therein particles 406 of a water-soluble acid pH control agent. This substrate may be provided as a diaper insert or liner which may or may not be affixed to the diaper topsheet.

The water-insoluble flexible substrate used to deliver pH control agent in this embodiment can comprise any suitable material which will act as a carrier for the pH control agent. Thus the substrate can be in the form of cloth, a non-woven substrate, e.g., paper, a film, or a sponge structure. Such substrates can be constructed of, for example, cellulose fiber, polyolefins, polyesters, rayon, and the like.

The pH control agents utilized in the diaper insert include the same type of materials disclosed hereinbefore for use in other embodiments of this invention. The pH control agent can be combined with the flexible insert substrate in any manner which provides the pH control agent in releasable form. Thus pH control agent, in either solid or liquid form, can be admixed with the substrate material as the substrate is being formed. Alternatively the pH control agent can be added to, impregnated in or sprayed on the insert substrate after the substrate is formed.

Enough pH control agent is preferably added to the insert substrate to provide a total concentration of pH control agent in the absorbent articles of from about 1% to b 10% by weight of the article, and preferably from about 2% to 5% by weight of the article. The insert substrates themselves will generally comprise from about 1% to 30% by weight of pH control agent, more preferably from about 5% to 15% by weight.

The insert substrate will generally not be large enough to cover the entire area of the article topsheet. Preferably the insert will cover only from about 20% to 90% of the top surface area of the topsheet on which the insert substrate is placed. Thickness of the insert substrate can vary widely depending upon the substrate type and the amount and type of pH control agent it carries. Insert substrates useful herein will generally range in thickness from about 0.2 to 1.5 cm.

A particularly preferred embodiment for the pH control agent-containing insert substrate can be prepared by air-laying an admixture of wood pulp fibers and particles of pH control agent to form a flexible web structure. This structure can be used as is or may be overwrapped with a liquid previous, nonwoven substrate or film. Such an overwrap can comprise, for example, envelope tissue or polyolefins such as polypropylene topsheet material.

The insert substrate can be actually secured to the topsheet of the absorbent article in order to ensure that the insert is properly positioned once the absorbent article is applied to the wearer. Thus the insert may be glued to the topsheet or otherwise affixed using two-sided adhesive tape or similar attaching means. Alternatively the insert substrate may simply be positioned on the absorbent article topsheet at the time the article is applied and not affixed to the topsheet in any way.

The absorbent articles of the present invention, with their distinct zones containing pH control agent and hydrogel material, are further illustrated by the following examples:

EXAMPLE I

A disposable diaper product containing both a cellulose phosphate pH control agent and particles of a starch-acrylate hydrogel material is prepared. Such an article comprises an absorbent core positioned between a polyethylene backing sheet and a hydrophobic, liquid pervious non-woven rayon topsheet. The absorbent core comprises two layers, one of which is an hourglass-shaped primary core and the other of which is a smaller oval insert placed beneath the primary core.

The hourglass consists of a homogeneous blend of southern soft wood/pine fibers and fibrous phosphorylated cellulose ("cellulose phosphate") having an ion exchange capacity of about 3.5 meq./gram. The oval insert consists of a homogeneous blend of southern soft wood/pine fibers and particles (250 microns) of acrylic acid grafted starch hydrogel ("Sanwet IM-1000" from Sanyo Co. Ltd., Japan). The absorbent core with its two layers is overwrapped with tissue paper.

A more detailed description of such a disposable diaper product is set forth in Example III hereinafter. Substantially similar disposable diapers can be prepared by replacing the cellulose phosphate pH control agent with an equivalent amount of an acid phosphate salt or with a low molecular weight organic acid such as citric acid, adipic acid, azelaic acid, malic acid, tartaric acid, gluconic acid, glutaric acid, levulenic acid, glycolic acid, succinic acid, fumaric acid, pimelic acid, suberic acid, or sebacic acid.

EXAMPLE II

A disposable diaper product containing both an acidified polyacrylate pH control agent and a starch acrylate hydrogel material is prepared. As in Example I, such an article comprises an absorbent core positioned between a polyethylene backing sheet and a hydrophobic, non-woven rayon topsheet. The absorbent core comprises two layers, one of which is an hourglass-shaped primary core and the other of which is a smaller oval insert placed beneath the primary core.

The hourglass consists of a homogeneous blend of southern soft wood/pine fibers and particles (300 microns avg.) of a slightly cross-linked, completely unneutralized poly(acrylic acid) hydrogel material. (Aqualic 4R04K1 from Nippon Shokubai K.K. Co., Ltd., Japan). The oval insert consists of a homogeneous blend of southern soft wood/pine fibers and particles (250 microns) of acrylic acid grafted starch hydrogel ("Sanwet IM-1000" from Sanyo Co. Ltd., Japan). The absorbent core with its two layers is overwrapped with tissue paper.

A more detailed description of such a disposable diaper product is set forth in Example IV hereinafter.

EXAMPLE III

Leakage and skin pH measurement studies were conducted to determine the ability of diapers containing pH control agents and hydrogel absorbents to lower skin pH and to absorb discharged body fluid. In such testing, performance of the cellulose phosphate-containing diaper of Example I was compared with that of (1) a similar product containing no cellulose phosphate in the hourglass core and (2) a commercially available diaper product containing a 100% wood pulp fiber core with no pH control agent or hydrogel material. These diaper products are more fully described in Table I hereinafter.

TABLE I

|  | Example I Diaper | Control Diapers Hydrogel Only | No Hydrogel |
|---|---|---|---|
| Core Composition (%) | 11/76/13 CP/CF/San | 84/16 CF/San | 100 CF |
| Hourglass (%) | 20/80 CP/CF | 84/16 CF/San | 100 CF |
| Insert (%) | 71/29 CF/San | NA | NA |
| Total Product Weight (gms) | 48.9 | 42.5 | 52.5 |
| Absorb. Core w/Tissue (gms) | 34.9 | 33.2 | 43.6 |
| Absorb. Core w/o Tissue (gms) | 32.6 | 30.9 | 39.1 |
| Hourglass (gms) | 17.9 | NA | NA |
| Insert (gms) | 14.7 | NA | NA |
| Core Dimensions | | | |
| Hourglass: | | | |
| Length (cm) | 38.1 | 38.1 | 38.1 |
| Width (cm) | 21.6 | 21.6 | 26.7 |
| Crotch (cm) | 13.3 | 12.7 | 17.1 |
| Area (cm$^2$) | 602.6 | 602.6 | NA |
| Insert | | | |
| Length (cm) | 25.4 | NA | NA |
| Width (cm) | 13.3 | NA | NA |
| Core Shape | Oval | NA | NA |
| Area (cm$^2$) | 299.4 | NA | NA |
| Basis Weight: | | | |
| Hourglass (gm/cm$^2$) | 0.049 | 0.051 | NA |
| Insert (gm/cm$^2$) | 0.030 | NA | NA |
| Density: | | | |
| Hourglass (gm/cm$^3$) | 0.150 | 0.132 | 0.100 |
| Insert (gm/cm$^3$) | 0.180 | NA | NA |

CP = Cellulose phosphate
CF = Cellulose fiber
San = Sanwet 1M-1000 Starch acrylate hydrogel (about 75% neutralized)
NA = Not Applicable or Not Available In the leakage and skin pH measurement testing, diapers are worn by normal infants. The infants are allowed to play in a nursery school setting during the test. The diapers are left on the infants until leakage occurs. In order to speed up the test, aliquots of synthetic urine are added at predetermined intervals.

In the particular test of this example, 25 infants were initially impaneled and divided into three groups, with approximately ⅓ being tested with one of three test diapers on each of three consecutive days. In this manner, at the end of the test, each infant had been exposed to each diaper one time. On the last day of the study, panelists' skin pHs (undiapered and diapered) were obtained after failure of the leakage test diaper was achieved.

Results of the leakage test and subsequent skin pH measurements taken as part of the post-leakage skin pH study are set forth in Table II.

TABLE II

|  | Example I Diaper | Hydrogel Only | No Hydrogel |
|---|---|---|---|
| Leakage Test Results Total Amount of Fluid Added to Diaper at Failure (ml average) | 264.1 | 234.3 | 185.2 |
| Post Leakage Skin pH Study | | | |
| Number of Panelists | 7 | 5 | 7 |
| Undiapered Skin pH (avg) | 4.86 | 4.96 | 4.90 |
| Standard Deviation | 0.17 | 0.19 | 0.53 |
| Diapered Skin pH (avg) | 4.29 | 5.88 | 5.47 |
| Standard Deviation | 0.54 | 0.43 | 0.38 |
| pH Change* (avg) | −0.56 | 0.92 | 0.57 |
| Standard Deviation | 0.50 | 0.35 | 0.48 |

*pH Change = Diapered Skin pH − Undiapered Skin pH

The Table II leakage test data indicate that the fluid-holding capacity of the Example I diaper is not compromised by the acidic pH buffering capacity provided by the cellulose phosphate pH control agent in the hourglass core. This is surprising since laboratory data would indicate that about 15% less absorbent capacity is provided by the Sanwet hydrogel material in an acidic environment. The post-leakage skin pH data in Table II also demonstrate that a skin pH increase occurs with the control diapers containing no pH control agent whereas the Example I diaper produced a statistically significant decrease in skin pH. This suggests that the acidic diapers are able to deliver a low pH benefit to skin when sufficient moisture is available to allow interaction between the diaper core and the skin.

EXAMPLE IV

Using the polyacrylate-containing diaper of Example II, leakage and pH measurement studies were conducted in the same general manner as described in Example III. Products tested included (1) the Example II diaper, (2) a similar product containing no acidic polyacrylate in the hourglass core, and (3) a commercially available diaper product containing a 100% wood pulp fiber core with no pH control agent or hydrogel material. These diaper products are described in greater detail in Table III.

TABLE III

|  | Example II Diaper | Control Diaper Hydrogel Only | No Hydrogel |
|---|---|---|---|
| Core Composition | | | |
| Hourglass (%) | 55.4 | 55.4 | 100 |
| Insert (%) | 44.6 | 44.6 | |
| Hourglass | | | |
| Length (cm) | 38.1 | 38.1 | 38.1 |
| Width (cm) | 21.6 | 21.6 | 26.7 |
| Area (cm$^2$) | 602.6 | 602.6 | NA |
| Density (g/cms) | 0.150 | 0.150 | 0.100 |
| Total Weight (gms) | 18.30 | 18.30 | 43.6 |
| Wood Pulp Fiber (gms) | 14.70 | 15.00 | NA |
| Acidified Polyacrylate* (gms) | 4.00 | — | — |
| Acidified Polyacrylate* (%) | 21.9 | 0.0 | 0.0 |

TABLE III-continued

|  | Example II Diaper | Control Diaper Hydrogel Only | No Hydrogel |
|---|---|---|---|
| Starch Acrylate Hydrogel** (gms) | — | 2.75 | — |
| Starch Acrylate Hydrogel** (%) Insert | 0.0 | 15.0 | 0.0 |
| Length (cm) | 25.4 | 25.4 | NA |
| Width (cm) | 13.3 | 13.3 | NA |
| Area (cm$^2$) | 299.3 | 299.3 | NA |
| Density (g/cm$^3$) | 0.18 | 0.18 | NA |
| Total Weight (gms) | 14.7 | 14.7 | NA |
| Wood Pulp Fiber (gms) | 10.7 | 12.5 | NA |
| Starch Acrylate Hydrogel** (gms) | 4.0 | 2.2 | NA |
| Starch Acrylate Hydrogel** (%) Total Core | 27.2 | 15.0 | NA |
| Core Weight (gms) | 33.0 | 33.0 | 39.1 |
| Tissue (gms) | 2.3 | 2.3 | 4.5 |

Leakage and skin pH study test results for the Table III diapers are set forth in Table IV.
*Aqualic 4R04K1 from Nippon Shokubai K.K. Co., Ltd.
**Sanwet IM-1000 from Sanyo Co. Ltd.

TABLE IV

|  | Example II Diaper | No Hydrogel |
|---|---|---|
| Leakage Test Results Total Amount of Fluid Added to Diaper at Failure (mls. avg.) | 246 | 204 |
| Post Leakage Skin pH Study |  |  |
| Number of Panelists | 8 | 9 |
| Undiapered Skin pH (avg.) | 4.75 ± 0.24 | 4.77 ± 0.36 |
| Diapered Skin pH (avg.) | 3.80 ± 0.89 | 5.44 ± 0.68 |
| pH change* (avg.) | −0.95 ± 0.78 | +0.68 ± 0.67 |

*pH change = Diapered skin pH − Undiapered skin pH

The Table IV data also demonstrate that the acidic diaper performed about as well as the non-acid, starch acrylate hydrogel-containing diaper with respect to fluid absorption capacity. The skin pH measurements again demonstrate the impact of the acid core in lowering skin pH in the presence of discharged body fluids.

EXAMPLE V

To demonstrate the necessity of maintaining pH control agent and fluid-absorbing hydrogel in distinct zones within the diaper, pH measurements are made on diapers with double layer cores containing various amounts of pH control agent and highly neutralized hydrogel. In this study, circular 6.2 cm diameter patches of diapers are prepared with two-layered cores, each of which layers is 3 mm thick and each of which layers comprises 80% wood pulp fiber and 20% of either a highly neutralized polyacrylate hydrogel absorbent, an acidified polyacrylate hydrogel pH control agent or a mixture of these two types of hydrogels. These patches are soaked in four times their weight of a mixture synthetic urine, salts, urea and urease to simulate the used diaper environment. The pH average of five locations on the patches are measured as a function of time. Results are set forth in Table V.

TABLE V

| Sample No. | Layer Composition | pH (avg.) 0 Hour | 1 Hour | 2 Hours |
|---|---|---|---|---|
| 1 | Top = 20% Aqualic* Bottom = 20% Aqualic | 5.4 | 7.7 | 8.0 |
| 2 | Top = 10% Aqualic/10% Acid Aqualic** Bottom = 10% Aqualic/10% Acid Aqualic | 5.2 | 6.9 | 7.0 |
| 3 | Top = 20% Acid Aqualic Bottom = 20% Aqualic | 4.0 | 4.6 | 4.3 |

*Aqualic is a slightly cross-linked polyacrylate neutralized to the extent of about 75% and is marketed under the tradename Aqualic 4R04K1 by Nippon Shokubai K.K. Co. Ltd., Japan.
**Acid Aqualic is a slightly cross-linked, poly(acrylic acid) prepared by acidifying the polyacrylate material marketed under the tradename Aqualic 4R04K1 by Nippon Shokubai K.K. Co. Ltd., Japan.

The Table V data clearly show the effect of separating pH control agent and absorbent hydrogel in the diaper core. In Sample 1, the two layers of the diaper core are identical and contain no pH control agent. Diaper pH rises in the presence of the synthetic urine, urea and urease. In Sample 2, the two layers of the diaper core are also identical, each containing a homogeneous mixture of highly neutralized absorbing hydrogel and acidified hydrogel pH control agent. Although diaper pH is maintained at a lower level by this acid-containing diaper core, a significant pH rise is still observed. In Sample 3, the acidic hydrogel pH control agent and the highly neutralized fluid-absorbing hydrogel are kept in separate layers of the diaper core. This configuration serves to maintain diaper pH at significantly lower levels than do the configurations of Samples 1 and 2.

EXAMPLE VI

A flexible substrate suitable for use as a pH control agent-containing diaper insert is prepared by air-laying a web of cellulose fiber (airfelt), which web has dimensions of 10 inches (25.4 cm)×4.5 inches (11.4 cm)×0.20 inches (0.50 cm) and a density of about 0.1 g/cm$^3$. Polyacrylic acid (Acrysol LMW-45, 15% neutralized) is uniformly distributed throughout the substrate as a pH control agent by airlaying a dry mixture of the airfelt and particles (125 to 700 microns) of the pH control agent. The insert substrate thus contains about 94% by weight airfelt and 6% by weight of the polyacrylate pH control agent. The finished insert is prepared by wrapping this substrate in polypropylene diaper topsheet material (8 mils) and melt-bonding the overwrap at the ends.

An absorbent article of the present invention is prepared by positioning this insert substrate on top of the topsheet of a conventional hydrogel-containing diaper (e.g. ULTRA PAMPERS ®) which utilizes an absorbent core comprising particles of polyacrylate hydrogel material admixed with airfelt. In this manner, the polyacrylate pH control agent comprises about 1.2% by weight of the insert/diaper combination. Such an insert/diaper combination provides effective skin pH control without significant loss of absorbent capacity of the diaper.

Substantially similar absorbent articles are realized when, in the above-described insert substrate, the polyacrylate pH control agent is replaced with an equivalent amount of poly(vinyl-ether-maleic acid) [Gantrez AN-119], ethylene-maleic acid copolymer [EMA-1103] or combination of sodium dihydrogen phosphate and disodium hydrogen phosphate.

EXAMPLE VII

Using the leakage and skin pH tests as generally described in Example III, the effect of using a diaper liner similar to that of Example VI with a hydrogel-containing diaper is determined. A control diaper similar to the hydrogel-only diaper of Table I (containing a polyacrylate hydrogel instead of a starch acrylate hydrogel) is tested for both leakage and pH control in comparison with that same diaper having a pH control insert positioned on the diaper topsheet. Such an insert, similar in composition to that described in Example VI, contains 6% polyacrylate (15% neutralized) in an airfelt substrate. This insert is positioned on top of the topsheet of the control diaper and is then placed next to the wearer's skin when the diaper is applied.

Results of the leakage and skin pH testing is shown in Table VI.

TABLE VI

| | Control Diaper | Control plus Insert |
|---|---|---|
| Leakage Test Results Total Amount of Fluid Added to Diaper at Failure (mls. avg.) | 189 | 225 |
| Post Leakage Skin pH Study | | |
| Number of Panelists | 9 | 9 |
| Undiapered Skin pH (avg.) | 4.81 ± 0.31 | 4.79 ± 0.61 |
| Diapered Skin pH (avg.) | 5.62 ± 0.43 | 4.76 ± 0.75 |
| pH change* (avg.) | +0.81 ± 0.43 | −0.03 ± 0.83 |

*pH change = Diapered skin pH − Undiapered skin pH

The Table VI data demonstrate that the diaper with insert performed as well as, and in fact somewhat better than, the polyacrylate hydrogel-containing control diaper with respect to fluid absorption capacity. The skin pH measurements demonstrate the impact of the insert in lowering skin pH in the presence of discharged body fluids.

What is claimed is:

1. A disposable absorbent article useful for absorbing discharged body fluids while also reducing or preventing diaper rash, said absorbent article comprising
    (A) a liquid impervious backing sheet;
    (B) a relatively hydrophobic, liquid pervious topsheet;
    (C) a flexible absorbent core positioned between said backing sheet and said topsheet, said flexible absorbent core comprising hydrophilic fiber material and particles of a substantially water-insoluble, highly neutralized hydrogel material having at least 50% of its acidic functional groups neutralized with salt-forming cations; and
    (D) one or more pH control agents suitable for maintaining skin pH within the range of from about 3.0 to 5.5 in the presence of urine and feces;
said substantially water-insoluble, highly neutralized hydrogel particles and said pH control agents being non-uniformly distributed in distinct discrete zones within said absorbent article.

2. An article according to claim 1 wherein
    (A) said substantially water-insoluble, highly neutralized hydrogel material is selected from acrylic acid grafted starch, polyacrylates, isobutylene maleic anhydride copolymers, and mixtures of these hydrogel materials; and
    (B) said pH control agents are selected from non-toxic, non-irritating low molecular weight organic and inorganic acids; non-toxic, non-irritating high molecular weight polymeric acids and ion exchange resins and fibers in the hydrogen form.

3. An article according to claim 2 wherein
    (A) the weight ratio of fiber to highly neutralized hydrogel in the absorbent core ranges from about 50:50 to 95:5;
    (B) the weight average particle size of the highly neutralized hydrogel material in said absorbent core ranges from about 50 microns to 1 mm; and
    (C) the pH control agent component comprises from about 1% to 30% by weight of said absorbent article.

4. An article according to claim 3 wherein said pH control agent is selected from citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid, and acid phosphate salts, carboxymethylcellulose, oxidized cellulose, sulfoethylcellulose and phosphorylated cellulose.

5. An article according to claim 3 wherein said pH control agent is selected from polyacrylic acid and its polyacrylate derivatives and poly(maleic acid) and its polymaleate derivatives.

6. An article according to claim 3 wherein said pH control agent is an ion-exchanging modified cellulose material in fiber form.

7. A disposable absorbent article useful for absorbing discharged body fluids while also preventing or reducing diaper rash, said absorbent article comprising
    (A) a liquid impervious backing sheet;
    (B) a relatively hydrophobic, liquid pervious topsheet having incorporated therein or thereon one or more pH control agents suitable for maintaining skin pH within the range of from about 3.0 to 5.5 in the presence of urine and feces; and
    (C) a flexible absorbent core positioned between said backing sheet and said topsheet, said flexible absorbent core consisting essentially of hydrophilic fiber material and particles of a substantially water-insoluble, highly neutralized hydrogel material having at least 50% of its acidic functional groups neutralized with salt-forming cations.

8. An article according to claim 7 wherein
    (A) said substantially water-insoluble, highly neutralized hydrogel material is selected from acrylic acid grafted starch, polyacrylates, isobutylene maleic anhydride copolymers, and mixtures of these hydrogel materials;
    (B) the weight ratio of fiber to highly neutralized hydrogel in the absorbent core ranges from about 50:50 to 95:5;
    (C) the weight average particle size of the highly neutralized hydrogel material in said adsorbent core ranges from about 50 microns to 1 mm; and
    (D) the pH control agent component comprises from about 5% to 15% by weight of said absorbent article.

9. An article according to claim 8 wherein said pH control agent is selected from citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid, and acid phosphate salts, carboxymethylcellulose, oxidized cellulose, sulfoethylcellulose and phosphorylated cellulose.

10. A disposable absorbent article useful for absorbing discharged body fluids while also preventing or reducing diaper rash, said absorbent article comprising
(A) a liquid impervious backing sheet;
(B) a relatively hydrophobic, liquid pervious topsheet; and
(C) a flexible absorbent core positioned between said backing sheet and said topsheet, said flexible absorbent core consisting essentially of
  (i) hydrophilic fiber material;
  (ii) particles of substantially water-insoluble, highly neutralized hydrogel material distributed within at least a portion of said hydrophilic fiber material, said highly neutralized hydrogel material having at least 50% of its acidic functional groups neutralized with salt-forming cations; and
  (iii) one or more pH control agents suitable for maintaining skin pH within the range of from about 3.0 to 5.5 in the presence of urine and feces;
said substantially water-insoluble, highly neutralized hydrogel particles and said pH control agents being non-uniformly distributed in distinct discrete zones within said flexible absorbent core.

11. An article according to claim 10 wherein
(A) said substantially water-insoluble, highly neutralized hydrogel material is selected from acrylic acid grafted starch, polyacrylates, isobutylene maleic anhydride copolymers, and mixtures of these hydrogel materials;
(B) the weight ratio of fiber to hydrogel in the absorbent core ranges from about 50:50 to 95:5;
(C) the weight average particle size of the highly neutralized hydrogel material in said absorbent core ranges from about 50 microns to 1 mm; and
(D) the pH control agent component comprises from about 5% to 15% by weight of said absorbent article.

12. An article according to claim 11 wherein said pH control agent is selected from citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid, acid phosphate salts, carboxymethylcellulose, oxidized cellulose, sulfoethylcellulose and phosphorylated cellulose.

13. An article according to claim 11 wherein said pH control agent is selected from polyacrylic acid and its polyacrylate derivatives and poly(maleic acid) and its polymaleate derivatives.

14. An article according to claim 11 wherein said pH control agent is an ion-exchanging modified cellulose material in fiber form.

15. An article according to claim 11 wherein the thickness of said absorbent core ranges from about 5 mm to 20 mm.

16. A disposable absorbent article useful for absorbing discharged body fluids while also preventing or reducing diaper rash, said absorbent article comprising
(A) a liquid impervious backing sheet;
(B) a relatively hydrophobic, liquid pervious topsheet; and
(C) a flexible absorbent core positioned between said backing sheet and said topsheet, said core at least one distinct hydrogel-containing layer and at least one of distinct pH control agent-containing layer; wherein
  (i) said hydrogel-containing layer consists essentially of
    (a) hydrophilic fiber material; and
    (b) particles of substantially water-insoluble, highly neutralized hydrogel material distributed within at least a portion of said hydrophilic fiber material, said highly neutralized hydrogel material having at least 50% of its acidic functional groups neutralized with salt-forming cations; and
  (ii) said pH control agent-containing layer consists essentially of
    (a) hydrophilic fiber material; and
    (b) one or more pH control agents suitable for maintaining skin pH within the range of from about 3.0 to 5.5 in the presence of urine and feces.

17. An article according to claim 16 wherein said absorbent core comprises a third distinct layer consisting essentially of hydrophilic fiber material with substantially no hydrogel or pH control agent present, said third distinct layer being positioned between said highly neutralized hydrogel-containing layer and said pH control agent-containing layer.

18. An article according to claim 16 wherein
(A) said substantially water-insoluble, highly neutralized hydrogel material is selected from acrylic acid grafted starch, polyacrylates, isobutylene maleic anhydride copolymers, and mixtures of these hydrogel materials;
(B) the weight ratio of fiber to hydrogel in the absorbent core ranges from about 50:50 to 95:5;
(C) the weight average particle size of the highly neutralized hydrogel material in said absorbent core ranges from about 50 microns to 1 mm; and
(D) the pH control agent component comprises from about 5% to 15% by weight of said absorbent article.

19. An article according to claim 18 wherein said pH control agent is selected from citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid, and acid phosphate salts, carboxymethylcellulose, oxidized cellulose, sulfoethylcellulose and phosphorylated cellulose.

20. An article according to claim 18 wherein said pH control agent is selected from polyacrylic acid and its polyacrylate derivatives and poly(maleic acid) and its polymaleate derivatives.

21. An article according to claim 18 wherein said pH control agent is an ion-exchanging modified cellulose material in fiber form.

22. A disposable absorbent article useful for absorbing discharged body fluids while also preventing or reducing diaper rash, said absorbent article comprising
(A) a liquid impervious backing sheet;
(B) a relatively hydrophobic, liquid pervious topsheet; and
(C) a flexible absorbent core comprising
  (i) hydrophilic fiber material;
  (ii) substantially water-insoluble, highly neutralized hydrogel material having at least 50% of its acidic functional groups neutralized with salt-forming cations; and
  (iii) one or more pH control agents, suitable for maintaining skin pH within the range of from about 3.0 to 5.5 in the presence of urine and feces;

said highly neutralized hydrogel material and said pH control agent being non-uniformly distributed in distinct discrete zones of said core, said zones being defined by partitioning the flat surface of said absorbent core into at least one area of relatively high hydrogel concentration and at least one area of relatively high pH control agent concentration.

23. An article according to claim 22 wherein the front two-thirds section of said article contains substantially all of the highly neutralized hydrogel material within said article and wherein the rear one-third of the article contains substantially all of the pH control agent within said article.

24. An article according to claim 22 wherein
(A) said substantially water-insoluble, highly neutralized hydrogel material is selected from acrylic acid grafted starch, polyacrylates, isobutylene maleic anhydride copolymers, and mixtures of these hydrogel materials;
(B) the weight ratio of fiber to highly neutralized hydrogel in the absorbent core ranges from about 50:50 to 95:5;
(C) the weight average particle size of the highly neutralized hydrogel material in said absorbent core ranges from about 50 microns to 1 mm; and
(D) the pH control agent component comprises from about 5% to 15% by weight of said absorbent article.

25. An article according to claim 24 wherein said pH control agent is selected from citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid, and acid phosphate salts, carboxymethylcellulose, oxidized cellulose, sulfoethylcellulose and phosphorylated cellulose.

26. An article according to claim 24 wherein said pH control agent is selected from polyacrylic acid and its polyacrylate derivatives and poly(maleic acid) and its polymaleate derivatives.

27. An article according to claim 24 wherein said pH control agent is an ion-exchanging modified cellulose material in fiber form.

28. A disposable absorbent article useful for absorbing discharged body fluids while also preventing or reducing diaper rash, said absorbent article comprising
(A) a liquid impervious backing sheet;
(B) a relatively hydrophobic, liquid pervious topsheet;
(C) a flexible absorbent core positioned between said backing sheet and said topsheet, said flexible absorbent core consisting essentially of
(i) hydrophilic fiber material; and
(ii) particles of substantially water-insoluble, highly neutralized hydrogel material distributed within at least a portion of said hydrophilic fiber material, said highly neutralized hydrogel material having at least 50% of its acidic functional groups neutralized with salt-forming cations; and
(D) a flexible, water-insoluble substrate positioned between said topsheet and the skin of the wearer of the article, said substrate containing one or more pH control agents suitable for maintaining the wearer's skin pH within the range of from about 3.0 to 5.5 in the presence of urine and feces.

29. An article according to claim 28 wherein
(A) said substantially water-insoluble, highly neutralized hydrogel material is selected from acrylic acid grafted starch, polyacrylates, isobutylene maleic anhydride copolymers, and mixtures of these hydrogel materials;
(B) the weight ratio of fiber to hydrogel in the absorbent core ranges from about 50:50 to 95:5;
(C) the weight average particle size of the highly neutralized hydrogel material in said absorbent core ranges from about 50 microns to 1 mm; and
(D) the pH control agent component in the flexible substrate comprises from about 1% to 10% by weight of said absorbent article.

30. An article according to claim 29 wherein said pH control agent is selected from citric acid, adipic acid, azelaic acid, malic acid, tartaric acid, gluconic acid, glutaric acid, levulenic acid, glycolic acid, succinic acid, fumaric acid, pimelic acid, suberic acid, sebacic acid, acid phosphate salts, carboxymethyl cellulose, oxidized cellulose, sulfoethylcellulose and phosphorylated cellulose.

31. An article according to claim 29 wherein said pH control agent is selected from polyacrylic acid and its polyacrylate derivatives and poly(maleic acid) and its polymaleate derivatives.

32. An article according to claim 29 wherein the flexible substrate is affixed to the topsheet of the absorbent article.

33. An article according to claim 29 wherein the flexible substrate is not affixed to the topsheet of the absorbent article.

34. An article according to claim 29 wherein the flexible substrate comprises a material selected from cellulose fibers, polyolefins, polyesters and rayon.

35. A disposable diaper useful for absorbing discharged body fluids while also preventing or reducing diaper rash, said diaper comprising
(A) a liquid impervious polyolefin backing sheet; (B) a relatively hydrophobic, liquid pervious topsheet;
(C) a flexible absorbent core positioned between said backing sheet and said topsheet, said flexible absorbent core consisting essentially of
(i) wood pulp fibers, and
(ii) particles of substantially water-insoluble, slightly cross-linked, highly neutralized polyacrylate hydrogel material distributed within at least a portion of said wood pulp fibers, said polyacrylate hydrogel material having at least 50% of its acidic functional groups neutralized with salt-forming cations, and
(D) a flexible air-laid web of wood pulp fibers positioned as an insert between said topsheet and the skin of the wearer of the diaper, said substrate having distributed therein or thereon one or more pH control agents selected from polyacrylic acid and its polyacrylate derivatives, poly(maleic acid) and its polymaleate derivatives, and acid phosphate salts, said pH control agents being present in an amount suitable for maintaining the wearer's skin pH within the range of from about 3.0 to 5.5 in the presence of urine and feces.

36. A diaper according to claim 35 wherein said insert is overwrapped with a liquid pervious nonwoven substrate or film comprising envelope tissue or polyolefin.

37. A diaper according to claim 35 wherein said insert covers from about 20% to 90% of the diaper topsheet top surface area.

38. A diaper according to claim 37 wherein said insert has a thickness of from about 0.2 to 1.5 cm.

39. A diaper according to claim 38 wherein pH control agent is present in said insert to the extent that pH control agent comprises from about 5 to 15% by weight of the insert and from about 2% to 5% by weight of the diaper.

* * * * *

UNITED STATES PATENT AND TRADEMARK OFFICE
CERTIFICATE OF CORRECTION

PATENT NO. : 4,685,909
DATED : August 11, 1987
INVENTOR(S) : Ronald W. Berg, Robert L. Stewart.

It is certified that error appears in the above-identified patent and that said Letters Patent are hereby corrected as shown below:

Column 2, line 50, "not" should be --now--.

Column 11, line 27, "to b 10%" should be --to 10%--.

Column 11, line 47, "previous" should be --pervious--.

Column 13, line 55 and 56, "failure (ml average)" should be at the left margin.

Signed and Sealed this

Second Day of February, 1988

Attest:

DONALD J. QUIGG

Attesting Officer

Commissioner of Patents and Trademarks